(12) United States Patent
Feger

(10) Patent No.: US 6,589,441 B1
(45) Date of Patent: Jul. 8, 2003

(54) HIGH VOLTAGE, HIGHLY CONDUCTIVE ELECTROLYTE FOR ELECTROLYTIC CAPACITORS

(75) Inventor: Christopher Feger, Easley, SC (US)

(73) Assignee: Pacesetter, Inc., Sunnyvale, CA (US)

(*) Notice: Subject to any disclaimer, the term of this patent is extended or adjusted under 35 U.S.C. 154(b) by 114 days.

(21) Appl. No.: 09/812,328

(22) Filed: Mar. 19, 2001

(51) Int. Cl.$^7$ .............................................. H01G 9/035
(52) U.S. Cl. ........................ 252/62.2; 361/506; 361/504; 607/5; 429/326; 429/339; 429/341; 429/337; 429/329; 429/433
(58) Field of Search ................... 252/62.2; 361/506, 361/504; 607/5; 429/326, 339, 341, 433, 337, 329

(56) References Cited

U.S. PATENT DOCUMENTS

| | | | |
|---|---|---|---|
| 5,111,365 A | 5/1992 | Dapo | 361/506 |
| 5,131,388 A | 7/1992 | Pless et al. | 128/419 D |
| 5,519,567 A | 5/1996 | Dapo | 361/506 |

Primary Examiner—C. Melissa Koslow
(74) Attorney, Agent, or Firm—Steven M. Mitchell

(57) ABSTRACT

The present invention is directed to a high voltage, highly conductive electrolyte for use in electrolytic capacitors and to an electrolytic capacitor impregnated with the electrolyte of the present invention for use in an implantable cardioverter defibrillator (ICD). The electrolyte according to the present invention is composed of a two solvent mixture of ethylene glycol and N-methylformamide; a combination of hypophosphorous acid, boric acid and an aliphatic dicarboxylic acid of carbon chain length from eight to twelve, such as azelaic, sebacic, or brassylic acid; an amine including ammonia, ammonium hydroxide, diethylamine, dimethylamine, triethylamine, or triethanolamine; and a nitro-substituted aromatic compound as a degassing agent, such as 3'-nitroacetophenone. Anhydrous ammonia may also be added to neutralize the solution. In an alternative embodiment of the electrolyte of the present invention, the ethylene glycol/NMF two solvent mixture can be substituted with 1,2-propanediol, using γ-butyrolactone as a cosolvent with or without NMF. The electrolyte of the present invention will allow the construction of multi-anode capacitors with low equivalent series resistance (ESR), which will have superior energy density and delivery, while being thinner due to fewer spacer and cathode layers with the same number of anodes. This resultant capacitor, when incorporated into an ICD, will reduce the size and thickness of the overall device.

37 Claims, 2 Drawing Sheets

HIGH VOLTAGE, HIGHLY CONDUCTIVE ELECTROLYTE FOR ELECTROLYTIC CAPACITORS

BACKGROUND OF THE INVENTION

1. Field of the Invention

The present invention is directed to a high voltage, highly conductive electrolyte for use in electrolytic capacitors and to an electrolytic capacitor impregnated with the electrolyte of the present invention for use in an implantable cardioverter defibrillator (ICD).

2. Related Art

Compact, high voltage capacitors are utilized as energy storage reservoirs in many applications, including implantable medical devices. These capacitors are required to have a high energy density since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

Implantable Cardioverter Defibrillators, such as those disclosed in U.S. Pat. No. 5,131,388, incorporated herein by reference, typically use two electrolytic capacitors in series to achieve the desired high voltage for shock delivery. For example, an implantable cardioverter defibrillator may utilize two 350 to 400 volt electrolytic capacitors in series to achieve a voltage of 700 to 800 volts.

Electrolytic capacitors are used in ICDs because they have the most nearly ideal properties in terms of size, reliability and ability to withstand relatively high voltage. Conventionally, such electrolytic capacitors include an etched aluminum foil anode, an aluminum foil or film cathode, and an interposed kraft paper or fabric gauze separator impregnated with a solvent-based liquid electrolyte. While aluminum is the preferred metal for the anode plates, other metals such as tantalum, magnesium, titanium, niobium, zirconium and zinc may be used. A typical solvent-based liquid electrolyte may be a mixture of a weak acid and a salt of a weak acid, preferably a salt of the weak acid employed, in a polyhydroxy alcohol solvent. The electrolytic or ion-producing component of the electrolyte is the salt that is dissolved in the solvent. The entire laminate is rolled up into the form of a substantially cylindrical body, or wound roll, that is held together with adhesive tape and is encased, with the aid of suitable insulation, in an aluminum tube or canister. Connections to the anode and the cathode are made via tabs. Alternative flat constructions for aluminum electrolytic capacitors are also known, comprising a planar, layered, stack structure of electrode materials with separators interposed therebetween, such as those disclosed in the above-mentioned U.S. Pat. No. 5,131,388.

The capacitance of an electrolytic capacitor is provided by the anodes. The paper separator and the cathode serve important roles in realizing the full capacitance of the anodes. A clear strategy for increasing energy density in the capacitor is to minimize the volume taken up by the paper and cathode foil and maximize the number of anodes, thus reducing the size of the device. This may be achieved by using a multi-anode stack configuration. For example, a multi-anode stack consists of a number of units of: a cathode, a paper spacer, two or more anodes, a paper spacer and a cathode; with neighboring units sharing the cathode between them. However, to charge and discharge the inner anodes (furthest from the cathode) charge must flow through the outer anodes. With typical anode foil, the path through an anode is quite tortuous and results in a high equivalent series resistance (ESR) for a multi-anode configuration. Thus, ESR increases as more anodes are placed together in the stack. To combat this problem, it has been suggested to provide very low resistivity electrolytes which may be used in a multi-anode configuration without an excessive ESR increase.

U.S. Pat. No. 5,111,365 to Dapo discloses an electrolytic capacitor provided with a low resistivity electrolyte. The disclosed electrolytic capacitor consists of aluminum anode and cathode members separated by an insulating spacer impregnated with an electrolyte consisting of a solution containing, (1) 50%–70% by weight of N-methylformamide; (2) up to 30% by weight of 2-methoxyethanol, 2-ethoxyethanol, ethylene glycol or 1,2-propylene glycol; (3) 12–20% by weight of an aromatic dicarboxylic acid selected from the group consisting of isophthalic acid and terephthalic acid; (4) from 4%–10% by weight of dimethylamine or monomethylamine, the ratio of the amine to the dicarboxylic acid being less than 2.00:1 and greater than 1.67:1; (5) up to 0.5% by weight of pelargonic acid; (6) up to 0.1% by weight of phosphoric acid; and (7) up to 8% by weight of water. These capacitors have been found to be useful at relatively low voltage applications, for example about 55 VDC.

U.S. Pat. No. 5,519,567 to Dapo discloses an electrolytic capacitor having aluminum anode and cathode members separated by a paper insulating spacer impregnated with an electrolyte solution containing (1) 1.50–4.00 wt. % of pelargonic acid; (2) 0.00–80.00 wt. % of N-methylformamide; (3) up to 0.05 wt. % of phosphoric acid; (4) 7.00–25.00 wt. % of isophthalic acid or an equivalent amount of terephthalic acid; (5) 1.50–15.00 wt. % of water; (6) an aliphatic amine sufficient to provide a pH of 7.2–8.5 and (7) ethylene glycol in an amount of about 0.00–70.00 wt. % of the solvent present, the mole % of the pelargonic acid being not greater than 5.5 mole % of all the acids present. Such a capacitor has been found particularly useful for the low-volt range of 0–100 VDC.

While these references disclose low resistivity electrolytes which may be used for low voltage capacitors, what is needed in the art is an electrolyte that provides low equivalent series resistance in an electrolytic capacitor operating at 400 volts, the useful energy for capacitors in implantable cardioverter defibrillators.

SUMMARY OF THE INVENTION

The present invention is directed to a high voltage, highly conductive electrolyte for use in electrolytic capacitors and to an electrolytic capacitor impregnated with the electrolyte of the present invention for use in an implantable cardioverter defibrillator (ICD). The electrolyte according to the present invention is composed of a two solvent mixture of ethylene glycol and N-methylformamide; a combination of hypophosphorous acid, boric acid and an aliphatic dicarboxylic acid of carbon chain length from eight to twelve, such as azelaic, sebacic, or brassylic acid; an amine including ammonia, ammonium hydroxide, diethylamine, dimethylamine, triethylamine, or triethanolamine; and a nitro-substituted aromatic compound as a degassing agent, such as 3'-nitroacetophenone. Anhydrous ammonia may also be added to neutralize the solution. A representative composition according to the present invention that displays the desired properties is: 82.1% by weight ethylene glycol, 4.1% by weight N-methylformamide, 0.2% by weight hypophosphorous acid, 5.7% by weight azelaic acid, 1.0% by weight boric acid, 1.0% by weight 3'-Nitroacetophenone, 1.5% by weight ammonium hydroxide (28–30% w/w), 0.8% by weight anhydrous ammonia and 3.6% by weight water.

In an alternative embodiment of the electrolyte of the present invention, the ethylene glycol/NMF two solvent mixture can be substituted with 1,2-propanediol, using γ-butyrolactone as a cosolvent with or without NMF. A representative composition according to this embodiment of the present invention that displays the desired properties is: 55.5% by weight 1,2-propanediol, 21.1% by weight γ-butyrolactone and 12.0% by weight N-methylformamide (NMF), 5.0% azelaic acid, 0.8% boric acid, 0.8% 3'-Nitroacetophenone, 2.3% by weight triethylamine and 2.5% water.

The electrolyte according to the present invention produces a low ESR multi-anode capacitor when combined with appropriate cathodes, spacers and etched and formed anodes at 400 volts, the useful energy for capacitors in implantable cardioverter defibrillators This electrolyte will allow the construction of multi-anode capacitors with low equivalent series resistance (ESR), which will have superior energy density and delivery, while being thinner due to fewer spacer and cathode layers with the same number of anodes. This resultant capacitor, when incorporated into an ICD, will reduce the size and thickness of the overall device, and allow for greater patient comfort, in addition to superior therapy.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENTS

The present invention is directed to a high voltage, highly conductive electrolyte for electrolytic capacitors and to an electrolytic capacitor impregnated with the electrolyte of the present invention for use in an ICD. In particular, the present invention is directed to a very low resistivity electrolyte which may be used in a multi-anode configuration without an excessive ESR increase. The electrolyte according to the present invention may be used in a capacitor operating at 400 VDC, the useful energy for capacitors in implantable cardioverter defibrillators.

Preferred embodiments of the present invention are now described. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

The electrolyte of the present invention is composed of a two solvent mixture of 50–90% by weight ethylene glycol and 3–40% by weight N-methylformamide (NMF); a combination of 0–1% by weight hypophosphorous acid, 0–3% by weight boric acid and 3–10% by weight of an aliphatic dicarboxylic acid of carbon chain length from eight to twelve, such as azelaic, sebacic, or brassylic acid; 1–4% by weight of an amine including ammonia, ammonium hydroxide, diethylamine, dimethylamine, triethylamine, or triethanolamine; 0–3% by weight of a nitro-substituted aromatic compound as a degassing agent, such as 3'-nitroacetophenone; and 0–8% by weight water. The electrolyte may further comprise 0.4–1.2% by weight anhydrous ammonia to further neutralize the solution. A representative composition that displays the desired properties is: 82.1% ethylene glycol, 4.1% N-methylformamide, 0.2% hypophosphorous acid, 5.7% azelaic acid, 1.0% boric acid, 1.0% 3'-Nitroacetophenone, 1.5% ammonium hydroxide (28–30% w/w), 0.8% anhydrous ammonia, and 3.6% water. This composition provides an open cup scintillation voltage at 38° C. of 410 volts, a conductivity of 6.20 mS/cm at 37.5° C. (resistivity of 161 Ω-cm), a pH of 7.3, and water content of 5.3% by Karl Fischer titration.

Figure 1:
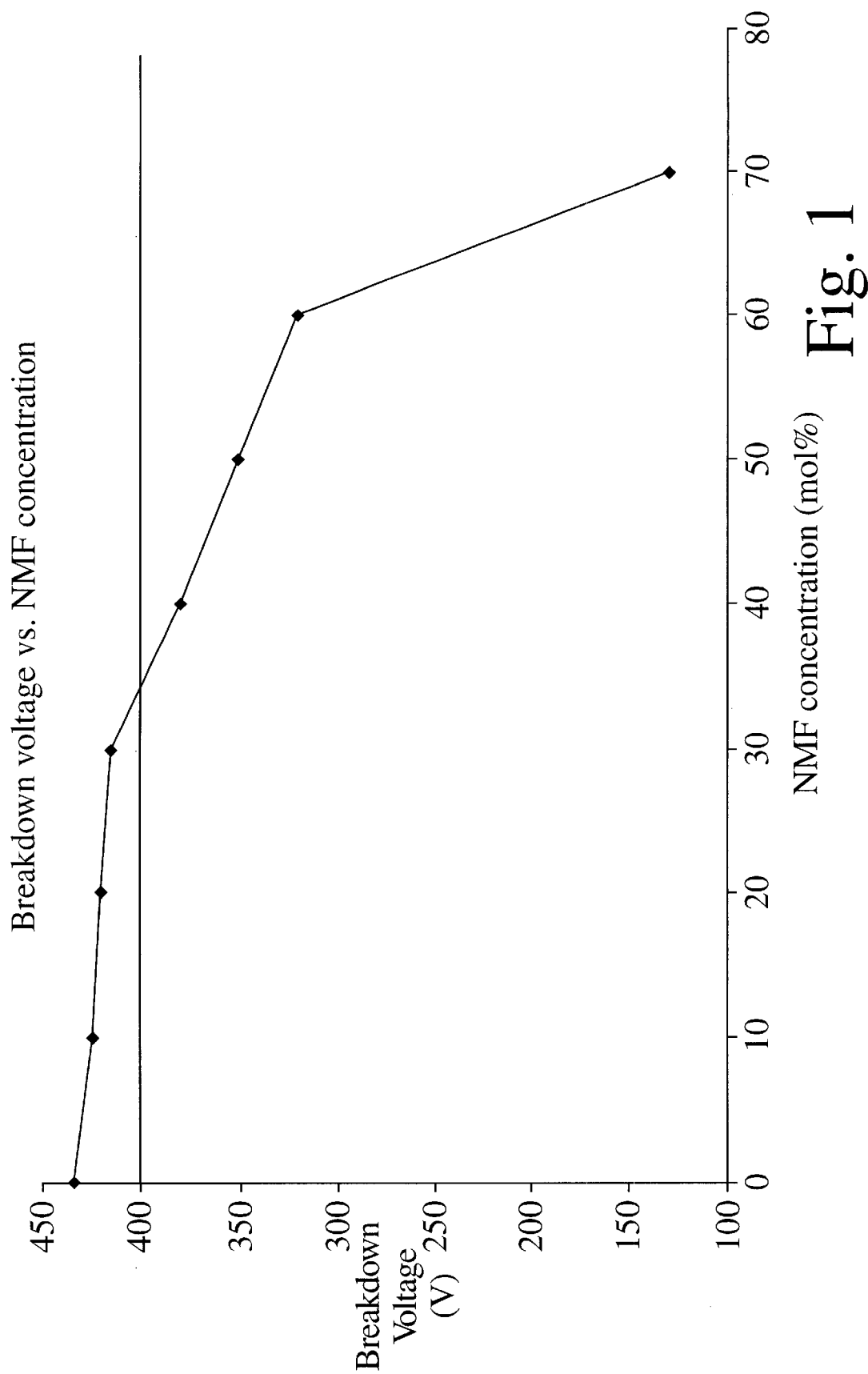
FIG. 1. is a graph showing the relationship of breakdown voltage to N-methylformamide (NMF)/ethylene glycol molar ratio for a pH leveled (pH=7.7–7.8) electrolyte according to the present invention.
Figure 2:
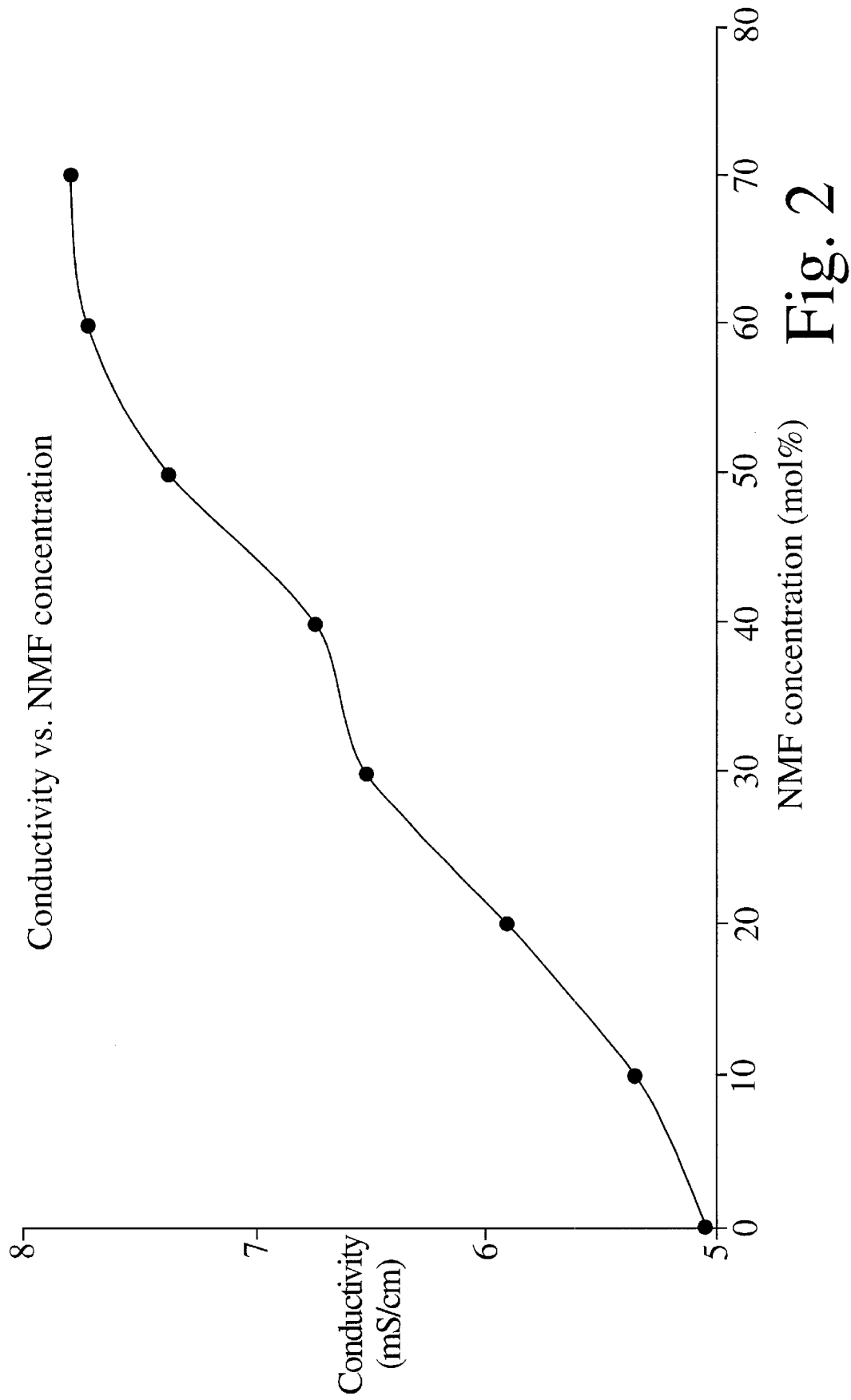
FIG. 2 is a graph showing the relationship of conductivity to N-methylformamide (NMF)/ethylene glycol molar ratio for a pH leveled (pH=7.7–7.8) electrolyte according to the present invention.

The graphs in FIGS. 1 and 2 show breakdown voltage vs. NMF/ethylene glycol molar ratios and conductivity vs. NMF/ethylene glycol molar ratios, respectively, for pH leveled (pH=7.7–7.8) samples. These graphs illustrate the effects of differing amounts of NMF on the properties of the resultant electrolytes.

The electrolyte according to the present invention provides low equivalent series resistance (ESR) in an electrolytic capacitor at 400 volts. The ESR in a multi-anode flat test capacitor went from 3.87 Ω with a conventional electrolyte to 2.36 Ω using an electrolyte according to the present invention.

In an alternative embodiment of the electrolyte of the present invention, the ethylene glycol/NMF two solvent mixture can be substituted with 1,2-propanediol, using γ-butyrolactone as a cosolvent with or without NMF. The preferred composition range for this electrolyte is 40–70% by weight 1,2-propanediol, 0–35% by weight }-butyrolactone and 2–35% by weight N-methylformamide (NMF); 0–1% hypophosphorous acid, 0–3% by weight boric acid and 3–10% by weight of an aliphatic dicarboxylic acid of carbon chain length from eight to twelve, such as azelaic, sebacic, or brassylic acid; 1–6% by weight of an amine including ammonia, ammonium hydroxide, diethylamine, dimethylamine, triethylamine, or triethanolamine; 0–3% by weight of a nitro-substituted aromatic compound as a degassing agent, such as 3'-nitroacetophenone; and 0–8% by weight water. The electrolyte may further comprise 0.4–1.2% by weight anhydrous ammonia to further neutralize the solution. A representative composition that displays the desired properties is: 55.5% by weight 1,2-propanediol, 21.1% by weight γ-butyrolactone and 12.0% by weight N-methylformamide (NMF), 5.0% azelaic acid, 0.8% boric acid, 0.8% 3'-Nitroacetophenone, 2.3% by weight triethylamine and 2.5% water.

A multi-anode flat capacitor according to the present invention is constructed of anode and cathode layers, stacked with a paper insulator or spacer between each layer. The anode layer is composed of a plurality of anode foils stacked together without any paper spacer, to form a high energy density multi-anode element. The anode and cathode layers are then grouped together in a parallel connection to produce sufficient capacitance for the intended function. This finished stack is inserted into a case with a geometry closely following the contour of the stack, and designed to minimize the space occupied inside the finished defibrillator.

Aluminum foil is preferred for the anode and cathode layers, because of its ability to produce a sufficient quality oxide layer, its conductive properties, and its wide commercial availability. Other valve metal foils conventionally utilized in electrolytic capacitors could also be used, including titanium, tantalum, magnesium, niobium, zirconium and zinc. Preferably, a strip of unetched, high purity (99.99%) aluminum foil with a cubicity of greater than 85% in the <100> direction is used. Such foils are well-known in the art and are readily available from commercial sources known to those skilled in the art.

The anode foil is etched in an aqueous halide based etch solution, typically a hydrochloric acid or sodium chloride solution, according to a conventional etch process; for example, U.S. Pat. No. 5,715,133 to Harrington et al. describes a suitable method of etching foil and is incorporated herein by reference in its entirety. The etch solution preferably consists of about 1.3% by weight sodium chloride, 3.5% by weight sodium perchlorate, 0.35% sodium persulfate, and deionized water. The etch solution preferably is heated to 60° C. to 95° C., more preferably 85° C. The foil is etched at a DC current density of about 0.01 A/cm$^2$ to 0.30 A/cm$^2$, preferably 0.15 A/cm$^2$. A charge of 20 to 100 coulombs per cm$^2$ is passed through the foil during the etching process, with about 50 coulombs/cm$^2$ preferred, which requires a time of about 2 minutes and 13 seconds to 11 minutes and 7 seconds, with about 5 minutes and 30 seconds preferred.

The foil is then removed from the etch solution and rinsed in deionized water. Then the tunnels formed during the initial etch are widened, or enlarged, in a secondary etch solution, typically an aqueous based nitrate solution, preferably between 1 to 20% aluminum nitrate, more preferably between 10 to 14% aluminum nitrate, with less than 1% free nitric acid. The etch tunnels are widened to an appropriate diameter by methods known to those in the art, such as that disclosed in U.S. Pat. No. 4,518,471 to Arora and U.S. Pat. No. 4,525,249 to Arora, entirely incorporated herein by reference.

After the etch tunnels have been widened, the foil is again rinsed with deionized water and dried. Finally, a barrier oxide layer may be formed onto one or both surfaces of the metal foil by placing the foil into an electrolyte bath and applying a positive voltage to the metal foil and a negative voltage to the electrolyte. The barrier oxide layer provides a high resistance to current passing between the electrolyte and the metal foils in the finished capacitor, also referred to as the leakage current. A high leakage current can result in the poor performance and reliability of an electrolytic capacitor. In particular, a high leakage current results in greater amount of charge leaking out of the capacitor once it has been charged.

The formation process consists of applying a voltage to the foil through an electrolyte such as boric acid and water or other solutions familiar to those skilled in the art, resulting in the formation of an oxide on the surface of the anode foil. The preferred electrolyte for formation is a 100–1000 µS/cm, preferably 500 µS/cm, citric acid concentration. In the case of an aluminum anode foil, the formation process results in the formation of aluminum oxide ($Al_2O_3$) on the surface of the anode foil. The thickness of the oxide deposited or "formed" on the anode foil is proportional to the applied voltage, roughly 10 to 15 Angstroms per applied volt.

The etched and formed anode foils are cut and the capacitor assembled as discussed above. A multi-anode capacitor stack according to the present invention consists of a number of units of: cathode, a paper spacer, two or more anodes, a paper spacer and cathode; with neighboring units sharing the cathode between them.

The electrolyte of the present invention is then prepared. Initially, the ethylene glycol and N-methylformamide (NMF) solvents are mixed and heated. As discussed above, in an alternative embodiment of the electrolyte of the present invention, the ethylene glycol/NMF two solvent mixture can be substituted with 1,2-propanediol, using γ-butyrolactone as a cosolvent with or without NMF. During heating, preferably at 60° C.–80° C., boric acid and an aliphatic dicarboxylic acid of carbon chain length from eight to twelve, such as azelaic acid, sebacic acid, or brassylic acid, are added to the solution and dissolved. The solution is then heated at 100° C.–110° C. for one hour. After heating, a nitro-substituted aromatic compound, such as 3'-nitroacetophenone, is added to the solution as a degassing agent and the solution is allowed to cool. At this point, ammonium hydroxide and hypophosphorous acid are added and thoroughly mixed in. The solution is then titrated with an amine including ammonia, diethylamine, triethylamine, or triethanolamine, to a pH range of 7–8. A representative composition according to the present invention consists of 82.1% by weight ethylene glycol, 4.1% by weight N-methylformamide, 0.2% by weight hypophosphorous acid, 5.7% by weight azelaic acid, 1.0% by weight boric acid, 1.0% by weight 3'-Nitroacetophenone, 1.5% by weight ammonium hydroxide (28–30%w/w), 0.8% by weight anhydrous ammonia and 3.6% by weight water.

The pre-assembled capacitor is then vacuum impregnated with the electrolyte of the present invention, by placing the capacitor in contact with the electrolyte and reducing the pressure to less than 50 cm Hg. The capacitor is held at this low pressure for 5 to 45 minutes with a preferred time of 30 minutes, and then pressure is restored, using the pressure to force the electrolyte mixture into the capacitor stack. The capacitor is then removed and placed in a 65 to 90° C. oven with a preferred temperature of 70° C. for a period of 2 to 24 hours, with a preferred time of 4 hours. The capacitor is then aged in a normal manner by applying the working voltage to the capacitor, allowing the capacitor to reach this voltage, and then allowing the current to decrease.

Electrolytic capacitors according to the present invention can be incorporated into implantable medical devices, such as implantable cardioverter defibrillators (ICDs), as would be apparent to one skilled in the art, as described in U.S. Pat. No. 5,522,851 issued to Fayram.

Having now generally described the invention, the same will be more readily understood through reference to the following examples which are provided by way of illustration, and are not intended to be limiting of the present invention.

EXAMPLES

Example 1

An electrolyte was prepared having the following formulation:

| | | |
|---|---|---|
| | Ethylene Glycol | 45.4 g |
| | N-methylformamide (NMF) | 43.1 g |
| | Azelaic Acid | 6.0 g |
| | Boric Acid | 1.0 g |
| | 3'-Nitroacetophenone | 1.1 g |
| | Ammonium hydroxide | 1.6 g |

The solvents were mixed and heated in a 200 mL beaker. At 80° C., the azelaic acid and boric acids were added and dissolved. The solution was heated to 100° C. and held for one hour at 100° C.–110° C. The hot plate was switched off and the nitroacetophenone was stirred in. The beaker was removed from the hot plate and allowed to cool. Once the temperature dropped below 40° C., the ammonia was added. A pH (at 38.8° C.) of 7.10 was observed and a conductivity of 4.00 mS/cm was obtained. An open cup scintillation voltage of approximately 430V was obtained.

Example 2

An electrolyte was prepared having the following formulation:

| | | |
|---|---|---|
| | Ethylene Glycol | 45.3 g |
| | N-methylformamide (NMF) | 43.0 g |
| | Nonanoic Acid | 3.8 g |
| | Azelaic Acid | 3.0 g |
| | Boric Acid | 1.0 g |
| | 3'-Nitroacetophenone | 1.0 g |
| | Ammonium hydroxide | 2.0 g |

The solvents and nonanoic acid were mixed in a 200 mL beaker and heated on a hot plate. At 100° C., the azelaic acid and boric acid were added and dissolved. The solution was heated to 120° C. and held for one hour at 120° C. The hot plate was switched off and the solution was allowed to cool to 100° C. were the nitroacetophenone was added. The beaker was removed from the hot plate and allowed to cool to room temperature, at which point the ammonia was added. A pH (at 23.8° C.) of 7.51 was observed and a conductivity of 4.36 mS/cm was obtained.

Example 3

An electrolyte was prepared having the following formulation:

| | | |
|---|---|---|
| | Ethylene Glycol | 81.5 g |
| | N-methylformamide (NMF) | 8.6 g |
| | Azelaic Acid | 6.0 g |
| | Boric Acid | 1.0 g |
| | 3'-Nitroacetophenone | 1.0 g |
| | Ammonium hydroxide | 1.6 g |

The solvents were mixed in a 200 mL beaker and heated with constant stirring. The mixture was heated to 85° C. and the azelaic acid and boric acid were added. The solution was then heated to 100° C. and held at 100° C.–110° C. for 1 hour. The solution was allowed to cool on the hot plate to 90° C. and the nitroacetophenone was added. The solution was then removed from the hot plate and allowed to cool to room temperature. At this point, the ammonia was stirred in. A pH (at 29.2° C.) of 6.00 was observed and a conductivity of 2.35 mS/cm was obtained.

After sparging in anhydrous ammonia to neutralize the solution, a pH (at 37.0° C.) of 7.73 was observed and a conductivity of 5.65 mS/cm was obtained. A breakdown voltage of 425–430V was observed at 38.0° C.

Example 4

An electrolyte was prepared having the following formulation:

| | | |
|---|---|---|
| | Ethylene Glycol | 72.5 g |
| | N-methylformamide (NMF) | 17.2 g |
| | Azelaic Acid | 6.0 g |
| | Boric Acid | 1.0 g |
| | 3'-Nitroacetophenone | 1.0 g |
| | Ammonium hydroxide | 1.0 g |

The solvents were mixed in a 200 mL beaker and heated with constant stirring. The mixture was heated to 85° C. and the azelaic acid and boric acid were added. The solution was then heated to 100° C. and held at 100° C.–110° C. for 1 hour. The solution was allowed to cool on the hot plate to 90° C. and the nitroacetophenone was added. The solution was then removed from the hot plate and allowed to cool to 30° C., when the ammonia was added. A pH (at 30.2° C.) of 6.31 was observed and a conductivity of 3.39 mS/cm was obtained.

After sparging in anhydrous ammonia to neutralize the solution, a pH (at 37.0° C.) of 7.79 was observed and a conductivity of 6.10 mS/cm was obtained. A breakdown voltage of 420–425V was observed at 37.9° C.

Example 5

An electrolyte was prepared having the following formulation:

| | | |
|---|---|---|
| | Ethylene Glycol | 63.4 g |
| | N-methylformamide (NMF) | 25.9 g |
| | Azelaic Acid | 6.0 g |
| | Boric Acid | 1.0 g |

-continued

| | |
|---|---|
| 3'-Nitroacetophenone | 1.0 g |
| Ammonium hydroxide | 1.6 g |

The solvents were mixed in a 200 mL beaker and heated with constant stirring. The mixture was heated to 85° C. and the azelaic acid and boric acid were added. The solution was then heated to 100° C. and held at 100° C.–110° C. for 1 hour. The hot plate was switched off and the solution was allowed to cool to 90° C., when the nitroacetophenone was added. The solution was then removed from the hot plate and allowed to below 30° C. At this point, the ammonia was added. A pH (at 29.6° C.) of 6.59 was observed and a conductivity of 3.74 mS/cm was obtained.

Anhydrous ammonia was then bubbled in to complete the reaction, a pH (at 35.8° C.) of 7.79 was observed and a conductivity of 6.37 mS/cm was obtained. A breakdown voltage of 415–420V was observed at 38.3° C.

Example 6

An electrolyte was prepared having the following formulation:

| | |
|---|---|
| Ethylene Glycol | 54.4 g |
| N-methylformamide (NMF) | 34.5 g |
| Azelaic Acid | 6.0 g |
| Boric Acid | 1.0 g |
| 3'-Nitroacetophenone | 1.0 g |
| Ammonium hydroxide | 1.6 g |

The solvents were mixed in a 200 mL beaker and heated with constant stirring. The mixture was heated to 85° C. and the azelaic acid and boric acid were added. The solution was then heated to 100° C. and held at 100° C.–110° C. for 1 hour. The hot plate was switched off and the solution was allowed to cool to 90° C., when the nitroacetophenone was added. The solution was then removed from the hot plate and allowed to below 30° C. At this point, the aqueous ammonia was added. A pH (at 29.6° C.) of 6.78 was observed and a conductivity of 4.93 mS/cm was obtained.

Anhydrous ammonia was then bubbled in to complete the reaction, a pH (at 35.1° C.) of 7.70 was observed and aconductivity of7.03 mS/cm was obtained. A breakdown voltage of 380–390V was observed at 38.0° C.

Example 7

An electrolyte was prepared having the following formulation:

| | |
|---|---|
| Ethylene Glycol | 45.3 g |
| N-methylformamide (NMF) | 43.1 g |
| Azelaic Acid | 6.0 g |
| Boric Acid | 1.0 g |
| 3'-Nitroacetophenone | 1.0 g |
| Ammonium hydroxide | 1.6 g |

The solvents were mixed in a 200 mL beaker and heated with constant stirring. The mixture was heated to 85° C. and the azelaic acid and boric acid were added and dissolved rapidly. The solution was then heated to 100° C. and held at 100° C.–110° C. for 1 hour. The hot plate was switched off and the solution was allowed to cool to 90° C., when the nitroacetophenone was added. After dissolution, the solution was removed from the hot plate and allowed to below 30° C. At this point, the ammonia was added. A pH (at 28.6° C.) of 6.91 was observed and a conductivity of 4.39 mS/cm was obtained.

Anhydrous ammonia was bubbled in to complete the reaction, a pH (at 32.9° C.) of 7.73 was observed and a conductivity of 6.61 mS/cm was obtained. A breakdown voltage of 350–375V was observed at 38.5° C.

Example 8

An electrolyte was prepared having the following formulation:

| | |
|---|---|
| Ethylene Glycol | 36.2 g |
| N-methylformamide (NMF) | 51.7 g |
| Azelaic Acid | 6.0 g |
| Boric Acid | 1.0 g |
| 3'-Nitroacetophenone | 1.0 g |
| Ammonium hydroxide | 1.6 g |

The solvents were mixed in a 200 mL beaker and heated with constant stirring. The mixture was heated to 85° C. and the azelaic acid and boric acid were added. The solution was then heated to 100° C. and held at 100° C.–110° C. for 1 hour. The hot plate was switched off and the solution was allowed to cool to 90° C., when the nitroacetophenone was added. The solution was then removed from the hot plate and allowed to below 30° C. At this point, the ammonia was added. A pH (at 28.8° C.) of 7.17 was observed and a conductivity of 5.48 mS/cm was obtained.

Anhydrous ammonia was added to complete the reaction, a pH (at 32.2° C.) of 7.73 was observed and a conductivity of 7.19 mS/cm was obtained. A breakdown voltage of 320–335V was observed at 38.6° C.

Example 9

An electrolyte was prepared having the following formulation:

| | |
|---|---|
| Ethylene Glycol | 27.2 g |
| N-methylformamide (NMF) | 60.4 g |
| Azelaic Acid | 6.0 g |
| Boric Acid | 1.0 g |
| 3'-Nitroacetophenone | 1.0 g |
| Ammonium hydroxide | 1.6 g |

The solvents were mixed in a 200 mL beaker and heated with constant stirring. The mixture was heated to 85° C. and the azelaic acid and boric acid were added. The solution was then heated to 100° C. and held at 100° C.–110° C. for 1 hour. The hot plate was switched off and the solution was allowed to cool to 90° C., when the nitroacetophenone was added. The solution was then removed from the hot plate and allowed to below 30° C. At this point, the ammonia was added. A pH (at 33.6° C.) of 7.34 was observed and a conductivity of 6.19 mS/cm was obtained.

Anhydrous ammonia was then added for final titration, a pH (at 34.1° C.) of 7.71 was observed and a conductivity of 7.44 mS/cm was obtained. A breakdown voltage of 130–135V was observed at 37.8° C.

Example 10

An electrolyte was prepared having the following formulation:

| | |
|---|---|
| Ethylene Glycol | 108.7 g |
| N-methylformamide (NMF) | 25.9 g |
| Azelaic Acid | 9.0 g |
| Boric Acid | 1.5 g |
| 3'-Nitroacetophenone | 1.5 g |
| Ammonium hydroxide | 2.4 g |

The solvents were mixed in a 200 mL beaker and heated with constant stirring. The mixture was heated to 100° C. and the azelaic acid and boric acid were added. The solution was then held at 105° C.–115° C. for 1 hour. The hot plate was switched off and the solution was allowed to cool to 90° C., when the nitroacetophenone was added. The solution was then removed from the hot plate and allowed to below 35° C. At this point, the ammonia was added. A pH (at 35.6° C.) of 6.29 was observed and a conductivity of 4.05 mS/cm was obtained.

Anhydrous ammonia was then added through a sparger for final titration, a pH (at 37.8° C.) of 6.98 was observed and a conductivity of 6.28 mS/cm was obtained.

Example 11

An electrolyte was prepared having the following formulation:

| | |
|---|---|
| 1,2 Propanediol | 233.3 g |
| γ-Butyrolactone | 88.8 g |
| N-methylformamide (NMF) | 50.4 g |
| Azelaic Acid | 21.0 g |
| Boric Acid | 3.5 g |
| 3'-Nitroacetophenone | 3.5 g |
| Water | 10.2 g |

The solvents were mixed in a 600 mL beaker and heated with constant stirring. The azelaic acid and boric acid were added when the solution reached 100° C. The solution was then heated at 110° C.–125° C. for 1 hour and allowed to cool. The hot plate was switched off and the solution was allowed to cool to 95° C., when the nitroacetophenone was added. The solution was then removed from the hot plate and allowed to cool to below 30° C. The water was added and stirred into the solution. Subsequently, 130.0 g of the mixture was removed and 3.0 g of triethylamine was added. After thorough mixing, the pH was 7.01 at 29.5° C. At 37° C., the conductivity was 1.95 mS/cm (513 Ω-cm resistivity) and the open cup breakdown voltage was 490 volts. Capacitance and effective series resistance values were obtained using an impedance measurement system comprising a gold-plated brass plate and a gold-plated brass cylinder. A porous polypropylene spacer was placed between the two plates and impregnated with the electrolyte. The frequency was varied to yield the results below:

| Frequency (hz) | ESR (Ω) | Capacitance (μF) |
|---|---|---|
| 50 | 4.762 | 248.61 |
| 60 | 4.026 | 237.32 |

| Frequency (hz) | ESR (Ω) | Capacitance (μF) |
|---|---|---|
| 100 | 2.600 | 212.32 |
| 120 | 2.259 | 205.04 |
| 200 | 1.597 | 189.06 |
| 300 | 1.280 | 178.60 |
| 400 | 1.124 | 171.95 |
| 500 | 1.033 | 167.10 |
| 600 | .9720 | 163.38 |
| 700 | .9286 | 160.30 |
| 800 | .8961 | 157.72 |
| 900 | .8706 | 155.81 |
| 1000 | .8801 | 153.57 |
| 1500 | .7882 | 146.7 |
| 2000 | .7568 | 142.2 |
| 2500 | .7379 | 139.0 |
| 3000 | .7282 | 136.7 |
| 3500 | .7163 | 134.8 |
| 4000 | .7095 | 133.3 |
| 4500 | .7044 | 132.1 |
| 5000 | .7002 | 131.2 |
| 6000 | .6939 | 129.8 |
| 7000 | .6896 | 129.1 |
| 8000 | .6862 | 128.8 |
| 9000 | .6837 | 128.9 |
| 10,000 | .6817 | 129.4 |
| 15,000 | .6758 | 136.7 |
| 20,000 | .6730 | 153.5 |
| 100,000 | .6804 | (0.1 μH) |

Example 12

An electrolyte was prepared having the following formulation:

| | |
|---|---|
| Ethylene Glycol | 108.7 g |
| γ-Butyrolactone | 37.7 g |
| N-methylformamide (NMF) | 25.9 g |
| Azelaic Acid | 9.0 g |
| Boric Acid | 1.5 g |
| 3'-Nitroacetophenone | 1.5 g |
| Water | 4.6 g |
| Triethylamine | 6.6 g |

The solvents were mixed in a 200 mL beaker and heated with constant stirring. The mixture was heated to 95° C. and the azelaic acid and boric acid were added. The solution was then heated to 100° C. and held at 10° C.–110° C. for 1 hour. The hot plate was switched off and the solution was allowed to cool to 95° C., when the nitroacetophenone was stirred in until it dissolved. The solution was then removed from the hot plate and allowed to below 30° C. The water was added and stirred into the solution. A pH (at 25.0° C.) of 5.48 was observed and a conductivity of 570 μS/cm was obtained.

Triethylamine was then added, a pH (at 29.8° C.) of 6.98 was observed and a conductivity of 2.80 mS/cm was obtained.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents. Additionally, all references cited herein, including journal articles or abstracts, published or corresponding U.S. or foreign patent applications, issued U.S. or foreign patents, or any other references, are each entirely incorporated by reference herein, including all data, tables, figures, and text presented in the cited references.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A high voltage, highly conductive electrolyte for electrolytic capacitors, comprising:
    ethylene glycol;
    N-methylformamide;
    hypophosphorous acid;
    boric acid;
    an aliphatic dicarboxylic acid of carbon chain length from eight to twelve;
    an amine; and
    a nitro-substituted aromatic compound as a degassing agent.

2. An electrolyte according to claim 1, wherein said aliphatic dicarboxylic acid is azelaic acid.

3. An electrolyte according to claim 1, wherein said aliphatic dicarboxylic acid is sebacic acid.

4. An electrolyte according to claim 1, wherein said aliphatic dicarboxylic acid is brassylic acid.

5. An electrolyte according to claim 1, wherein said amine is ammonia.

6. An electrolyte according to claim 1, wherein said amine is diethylamine.

7. An electrolyte according to claim 1, wherein said amine is dimethylamine.

8. An electrolyte according to claim 1, wherein said amine is triethylamine.

9. An electrolyte according to claim 1, wherein said amine is triethanolamine.

10. An electrolyte according to claim 1, wherein said nitro-substituted aromatic compound is 3'-nitroacetophenone.

11. A high voltage, highly conductive electrolyte for electrolytic capacitors, comprising ethylene glycol, N-methylformamide, hypophosphorous acid, azelaic acid, boric acid, 3'-Nitroacetophenone, ammonium hydroxide and anhydrous ammonia.

12. An electrolyte according to claim 11, comprising 50–95% by weight ethylene glycol, 3–40% by weight N-methylformamide, no more than 1% by weight hypophosphorous acid; 3–10% by weight azelaic acid, no more than 3% by weight boric acid, no more than 3% by weight 3'-Nitroacetophenone, 1–4% by weight ammonium hydroxide, 0.4–1.2% by weight anhydrous ammonia and 0–8% by weight water.

13. An electrolyte according to claim 11, comprising 82.1% by weight ethylene glycol, 4.1% by weight N-methylformamide, 0.2% by weight hypophosphorous acid; 5.7% by weight azelaic acid, 1.0% by weight boric acid, 1.0% by weight 3'-Nitroacetophenone, 1.5% by weight ammonium hydroxide, 0.8% by weight anhydrous ammonia and 3.6% by weight water.

14. An electrolytic capacitor impregnated with a high voltage, highly conductive electrolyte for electrolytic capacitors, comprising:
    ethylene glycol;
    N-methylformamide;
    hypophosphorous acid;
    boric acid;
    an aliphatic dicarboxylic acid of carbon chain length from eight to twelve;
    an amine; and
    a nitro-substituted aromatic compound as a degassing agent.

15. An electrolytic capacitor impregnated with a high voltage, highly conductive electrolyte for electrolytic capacitors, comprising ethylene glycol, N-methylformamide, hypophosphorous acid, azelaic acid, boric acid, 3'-Nitroacetophenone, ammonium hydroxide and anhydrous ammonia.

16. An implantable cardioverter defibrillator (ICD) comprising an electrolytic capacitor impregnated with a high voltage, highly conductive electrolyte for electrolytic capacitors, comprising:
    ethylene glycol;
    N-methylformamide;
    hypophosphorous acid;
    boric acid;
    an aliphatic dicarboxylic acid of carbon chain length from eight to twelve;
    an amine; and
    a nitro-substituted aromatic compound as a degassing agent.

17. An implantable cardioverter defibrillator (ICD) comprising an electrolytic capacitor impregnated with a high voltage, highly conductive electrolyte for electrolytic capacitors, comprising ethylene glycol, N-methylformamide, hypophosphorous acid, azelaic acid, boric acid, 3'-Nitroacetophenone, ammonium hydroxide and anhydrous ammonia.

18. A high voltage, highly conductive electrolyte for electrolytic capacitors, comprising:
    1,2-Propanediol;
    γ-Butyrolactone;
    hypophosphorous acid;
    boric acid;
    an aliphatic dicarboxylic acid of carbon chain length from eight to twelve;
    an amine; and
    a nitro-substituted aromatic compound as a degassing agent.

19. An electrolyte according to claim 18, further comprising N-methylformamide.

20. An electrolyte according to claim 18, wherein said aliphatic dicarboxylic acid is azelaic acid.

21. An electrolyte according to claim 18, wherein said aliphatic dicarboxylic acid is sebacic acid.

22. An electrolyte according to claim 18, wherein said aliphatic dicarboxylic acid is brassylic acid.

23. An electrolyte according to claim 18, wherein said amine is ammonia.

24. An electrolyte according to claim 18, wherein said amine is diethylamine.

25. An electrolyte according to claim 18, wherein said amine is dimethylamine.

26. An electrolyte according to claim 18, wherein said amine is triethylamine.

27. An electrolyte according to claim 18, wherein said amine is triethanolamine.

28. An electrolyte according to claim 18, wherein said nitro-substituted aromatic compound is 3'-nitroacetophenone.

29. A high voltage, highly conductive electrolyte for electrolytic capacitors, comprising 1,2-propanediol, γ-butyrolactone N-methylformamide, hypophosphorous acid, azelaic acid, boric acid, 3'-Nitroacetophenone and triethylamine.

30. An electrolyte according to claim 29, comprising 40–70% by weight 1,2-propanediol, no more than 35% by weight γ-butyrolactone, 2–35% by weight N-methylformamide (NMF), no more than 1% hypophosphorous acid, 3–10% azelaic acid, no more than 3% by weight boric acid, no more than 3% by weight 3'-Nitroacetophenone; 1–6% by weight triethylamine and no more than 8% by weight water.

31. An electrolyte according to claim 28, comprising 55.5% by weight 1,2-propanediol, 21.1% by weight γ-butyrolactone, 12.0% by weight N-methylformamide, 5.0% by weight azelaic acid, 0.8% by weight boric acid, 0.8% by weight 3'-Nitroacetophenone, 2.3% by weight triethylamine and 2.5% by weight water.

32. An electrolytic capacitor impregnated with a high voltage, highly conductive electrolyte for electrolytic capacitors, comprising:

1,2-Propanediol;

γ-Butyrolactone;

hypophosphorous acid;

boric acid;

an aliphatic dicarboxylic acid of carbon chain length from eight to twelve;

an amine; and a nitro-substituted aromatic compound as a degassing agent.

33. An electrolytic capacitor impregnated with a high voltage, highly conductive electrolyte for electrolytic capacitors according to claim 32, further comprising N-methylformamide.

34. An electrolytic capacitor impregnated with a high voltage, highly conductive electrolyte for electrolytic capacitors, comprising 1,2-propanediol, γ-butyrolactone N-methylformamide, hypophosphorous acid, azelaic acid, boric acid, 3'-Nitroacetophenone and triethylamine.

35. An implantable cardioverter defibrillator (ICD) comprising an electrolytic capacitor impregnated with a high voltage, highly conductive electrolyte for electrolytic capacitors, comprising:

1,2-Propanediol;

γ-Butyrolactone;

hypophosphorous acid;

boric acid;

an aliphatic dicarboxylic acid of carbon chain length from eight to twelve;

an amine; and a nitro-substituted aromatic compound as a degassing agent.

36. An implantable cardioverter defibrillator (ICD) comprising an electrolytic capacitor impregnated with a high voltage, highly conductive electrolyte for electrolytic capacitors according to claim 35, further comprising N-methylformamide.

37. An implantable cardioverter defibrillator (ICD) comprising an electrolytic capacitor impregnated with a high voltage, highly conductive electrolyte for electrolytic capacitors, comprising 1,2-propanediol, γ-butyrolactone N-methylformamide, hypophosphorous acid, azelaic acid, boric acid, 3'-Nitroacetophenone and triethylamine.

* * * * *